_United States Patent_ [19]

Lantzsch et al.

[11] Patent Number: 5,162,529
[45] Date of Patent: Nov. 10, 1992

[54] PROCESS FOR THE PREPARATION OF 5-HYDROXY-3,4,5,6-TETRAHYDRO-PYRIMIDINE DERIVATIVES

[75] Inventors: Reinhard Lantzsch, Wuppertal; Hermann Seifert, Bergisch Gladbach, both of Fed. Rep. of Germany

[73] Assignee: Bayer Aktiengesellschaft, Leverkusen, Fed. Rep. of Germany

[21] Appl. No.: 757,852

[22] Filed: Sep. 11, 1991

[30] Foreign Application Priority Data

Sep. 22, 1990 [DE] Fed. Rep. of Germany ....... 4030059

[51] Int. Cl.$^5$ .......................................... C07D 239/34
[52] U.S. Cl. .................................... 544/298
[58] Field of Search ......................... 544/298

[56] References Cited

FOREIGN PATENT DOCUMENTS 0320796 6/1989 European Pat. Off. .
1403732 8/1975 United Kingdom .

_Primary Examiner_—John M. Ford
_Attorney, Agent, or Firm_—Sprung Horn Kramer & Woods

[57] ABSTRACT

The invention relates to a new process for the preparation of 5-hydroxy-3,4,5,6-tetrahydro-pyrimidine derivatives of the general formula (I)

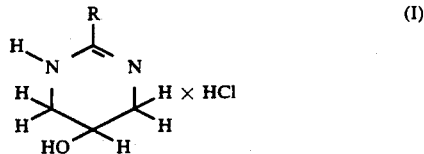

in which
R represents optionally substituted alkyl,
which is characterized in that amidines of the general formula (II),

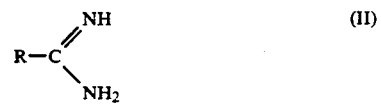

in which
R has the abovementioned meaning,
are reacted with epichlorohydrin of the formula (III)

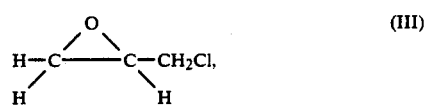

if appropriate in the presence of a diluent at temperatures between 0° C. and 150° C.

7 Claims, No Drawings

PROCESS FOR THE PREPARATION OF 5-HYDROXY-3,4,5,6-TETRAHYDRO-PYRIMIDINE DERIVATIVES

The invention relates to a new process for the preparation of 5-hydroxy-3,4,5,6-tetrahydro-pyrimidine derivatives which are known and which can be used as intermediates for the synthesis of insecticides.

It has been disclosed that certain 5-hydroxy-3,4,5,6-tetrahydro-pyrimidine derivatives such as, for example, 2-tert-butyl-5-hydroxy-3,4,5,6-tetrahydropyrimidine hydrochloride, are obtained when corresponding amidines (or their acid adducts) such as, for example, pivalamidine hydrochloride, are reacted with 1,3-diamino-2-propanol in the presence of diluents such as, for example, ethanol (compare EP-A 320,796).

A grave disadvantage of the known synthesis route is that it requires 1,3-diamino-2-propanol as starting substance, which can be prepared from epichlorohydrin and ammonia, but yield has been unsatisfactory to date (not more than approx. 55% of theory) (compare EP-A 359,956). Moreover, 1,3-diamino-2-propanol is prepared in a dilution which is relatively high for industrial processes. Working-up, isolation and purification of the product thus result in very high production costs which make such a process uneconomical since vast amounts of waste water are generated and vast amounts of ammonia and water have to be removed by distillation.

It has now been found that 5-hydroxy-3,4,5,6-tetrahydropyrimidine derivatives of the general formula (I)

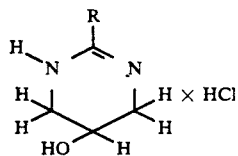

(I)

in which
R represents optionally substituted alkyl,
are obtained when amidines of the general formula (II)

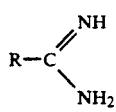

(II)

in which
R has the abovementioned meaning,
are reacted with epichlorohydrin of the formula (III)

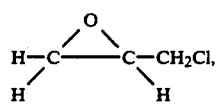

(III)

if appropriate in the presence of a diluent at temperatures between 0° C. and 150° C.

The selective course of the process according to the invention must be considered as surprising, since it was to be expected that amidines would react with epichlorohydrin on both nitrogen atoms. The formation of polymers, as is known from reactions of epichlorohydrin with diamines, was also to be expected. Finally, cyclisation to give five-membered cycles (hydroxymethylimidazolines) must also be taken into account.

Compared with the known method, the compounds of the formula (I) can be prepared with considerably greater ease and on the basis of readily accessible starting substances in very good yields and in high purity when the process according to the invention is used. The process according to the invention thus represents a valuable enrichment of the prior art.

In formulae (I) and (II), alkyl (R) represents straight-chain or branched alkyl having preferably 1 to 20, particularly preferably 1 to 10, especially 1 to 5, carbon atoms. The following may be mentioned by way of example: methyl, ethyl, n-propyl, i-propyl, n-butyl, i-butyl, s-butyl, t-butyl, n-pentyl, i-pentyl, s-pentyl and t-pentyl.

Alkyl (R) can contain one or more, preferably 1 to 3, identical or different substituents. Substituents from the series of the halogens, such as fluorine, chlorine or bromine, especially fluorine and chlorine, are preferred.

Alkyl (R) is preferably unsubstituted.

R in the general formulae preferably represents straight-chain or branched alkyl having 1 to 10 carbon atoms and which is optionally substituted by fluorine, chlorine and/or bromine.

R in the general formulae particularly preferably represents straight-chain or branched alkyl having 1 to 5 carbon atoms and which is optionally substituted by fluorine and/or chlorine.

R in the general formulae very particularly preferably represents t.-butyl, the t.-butyl group being preferably unsubstituted.

If, for example, pivalamidine and epichlorohydrin are used as starting substances, the course of the reaction in the process according to the invention can be represented by the following equation:

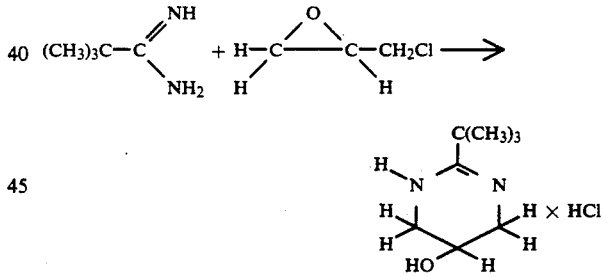

The amidines of the formula (II) which are to be used as starting substances in the process according to the invention have already been disclosed (compare EP-A 320,796).

Epichlorohydrin of the formula (III), which is furthermore to be employed as starting compound, is a known chemical for synthesis.

The process according to the invention is preferably carried out using diluents. Suitable diluents for this purpose are virtually all inert organic solvents. These include, for example, aliphatic and aromatic, optionally halogenated hydrocarbons such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

Preferred diluents are aprotic polar solvents, preferably from the series of the $C_1$-$C_4$-acyl-nitriles such as, for example, acetonitrile or propionitrile, and of the di(C$_1$-C$_4$)-alkyl ketones such as, for example, acetone, butanone and methyl isobutyl ketone.

When carrying out the process according to the invention, the reaction temperatures can be varied within a substantial range. In general, the process is carried out at temperatures from 0° C. to 150° C., preferably from 10° to 120° C., and particularly preferably between 20° and 100° C.

The process according to the invention is generally carried out under atmospheric pressure. However, it is also possible to carry out the process under increased or reduced pressure—in general, from 10 hPa to 10,000 hPa.

When carrying out the process according to the invention, the amounts of starting substances employed can be varied within a wide range without serious disadvantages.

For carrying out the process according to the invention, between 1 and 2 moles, in particular between 1.1 and 1.5 moles, of epichlorohydrin of the formula (III) are preferably employed per mole of amidine of the formula (II).

In a preferred embodiment of the process according to the invention, the amidine of the formula (II) is initially introduced into a diluent, and epichlorohydrin is added slowly, if appropriate at an increased temperature, preferably between 20° and 100° C. The reaction mixture is then stirred until the reaction is complete, in general at a increased temperature.

In general, the product of the formula (I) is obtained directly in crystalline form. Once cold, it can then be isolated by filtration with suction. However, the mixture can also be concentrated and the product which remains can be purified by treating with an organic solvent (compare the Preparation Examples).

The compounds of the formula (I) to be prepared by the process according to the invention can be used as intermediates for the preparation of insecticides (compare EP-A 320,796).

In the present text, all percentages are per cent by weight unless otherwise indicated.

PREPARATION EXAMPLES

Example 1

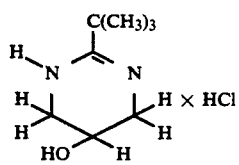

50 g of pivalamidine (81.6%/0.41 mol) are dissolved in 300 ml of acetonitrile and heated to 80° C., and 56 g (0.60 mol) of epichlorohydrin, dissolved in 50 ml of acetonitrile, are then added dropwise, with stirring. The reaction mixture is then heated at the boil for 6 hours. After cooling, the mixture is concentrated, the residue is stirred with 100 ml of acetonitrile, and the crystalline product is isolated by filtration with suction.

90 g of 5-hydroxy-2-tert-butyl-3,4,5,6-tetrahydro-pyrimidine hydrochloride (83.7%/96% of theory) are obtained in the form of colourless, highly hygroscopic crystals.

Example 2

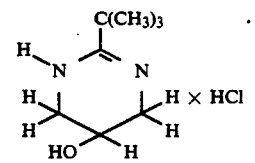

50 g of pivalamidine (81.6%/0.41 mol) are dissolved in 300 ml of butanone and 51 g (0.55 mol) of epichlorohydrin are steadily added dropwise at 20° C. to 25° C. The reaction mixture is heated at the boil for 6 hours with stirring and then cooled down. The product which has been obtained in the form of crystals is isolated by filtration with suction.

62.2 g of 5-hydroxy-2-tert-butyl-3,4,5,6-tetrahydropyrimidine hydrochloride (95%/76% of theory) are obtained in the form of colourless, highly hygroscopic crystals.

We claim:

1. Process for the preparation of 5-hydroxy-3,4,5,6-tetrahydro-pyrimidine derivatives of the general formula (I)

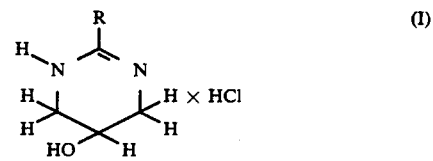

in which
R represents optionally substituted alkyl,
characterised in that amidines of the general formula (II)

in which
R has the abovementioned meaning,
are reacted with epichlorohydrin of the formula (III)

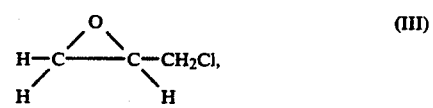

if appropriate in the presence of a diluent at temperatures between 0° C. and 150° C.

2. Process according to claim 1, where R represents alkyl having 1 to 10 carbon atoms and which is optionally substituted by fluorine, chlorine and/or bromine.

3. Process according to claim 1, where R represents t.-butyl.

4. Process according to claim 1, where an aprotic polar solvent is employed.

5. Process according to claim 1, where the process is carried out at temperatures from 10° to 120° C.

6. Process according to claim 1, where between 1 and 2 moles of epichlorohydrin of the formula (III) are employed per mole of amidine of the formula (II).

7. Process according to claim 1, where between 1.1 and 1.5 moles of epichlorohydrin are employed per mole of amidine of the formula (II).

* * * * *